United States Patent

Paul et al.

[11] Patent Number: 5,873,733
[45] Date of Patent: Feb. 23, 1999

[54] TRAINING UNIT FOR THE PACEMAKER EMERGENCY INTERVENTION SYSTEM USING MAGNETIC ENTRY CODE

[75] Inventors: Patrick J. Paul; David Prutchi, both of Lake Jackson, Tex.

[73] Assignee: Sulzer Intermedics Inc., Angleton, Tex.

[21] Appl. No.: 12,280

[22] Filed: Jan. 23, 1998

[51] Int. Cl.⁶ .................................................. A61N 1/37
[52] U.S. Cl. ............................... 434/262; 607/9; 607/27; 607/30; 607/32
[58] Field of Search ................................... 434/262, 265; 607/30

[56] References Cited

U.S. PATENT DOCUMENTS

| | | | |
|---|---|---|---|
| 4,091,549 | 5/1978 | Driller et al. | 35/17 |
| 4,830,006 | 5/1989 | Haluska et al. | 128/419 |
| 5,661,459 | 8/1997 | Belcher | 340/573 |
| 5,662,694 | 9/1997 | Lidman et al. | 607/60 |

OTHER PUBLICATIONS

Association for the Advancement of Medical Instrumentation; ISO/WD 14994, Implants for surgery—Cardiac pacemakers—Pacemaker emergency intervention system, Jul. 1997, 19 pages, Arlington, VA.

*Primary Examiner*—Robert A. Hafer
*Assistant Examiner*—David A. Fleming
*Attorney, Agent, or Firm*—John R. Merkling; Conley, Rose & Tayon

[57] ABSTRACT

A training unit generally includes a processor, a magnetic field sensor, a plurality of control switches, and a message and data output device. Placing a PEIS magnet, constructed in accordance with the ISOWD 14994 standard, adjacent to or in contact with the training unit activates the magnetic field sensor, a condition detectable by the processor. Activation of the switches determines which of three modes the training unit will operate. In an instructional mode, the process provides instructional messages to the operator via the message and data output device, which preferably includes a display and an audio speaker. In a coached mode, the training unit informs the operator when to place the magnet adjacent to or in contact with the training unit and when to remove the magnet in accordance with the timing intervals of the PEIS entry code. In a practice mode, the operator initiates and completes the entry code using a PEIS magnet without coaching. The processor detects the presence of the PEIS magnet, and determines whether the operator correctly performed the entry code correctly. If the operator completes the entry code in either the coached or practice modes, a simulated ECG waveform indicative of a patient's surface ECG upon successful completion of an entry code is shown on the display. Conversely, the training unit informs the operator of a failure by the operator to successfully complete the entry code.

26 Claims, 4 Drawing Sheets

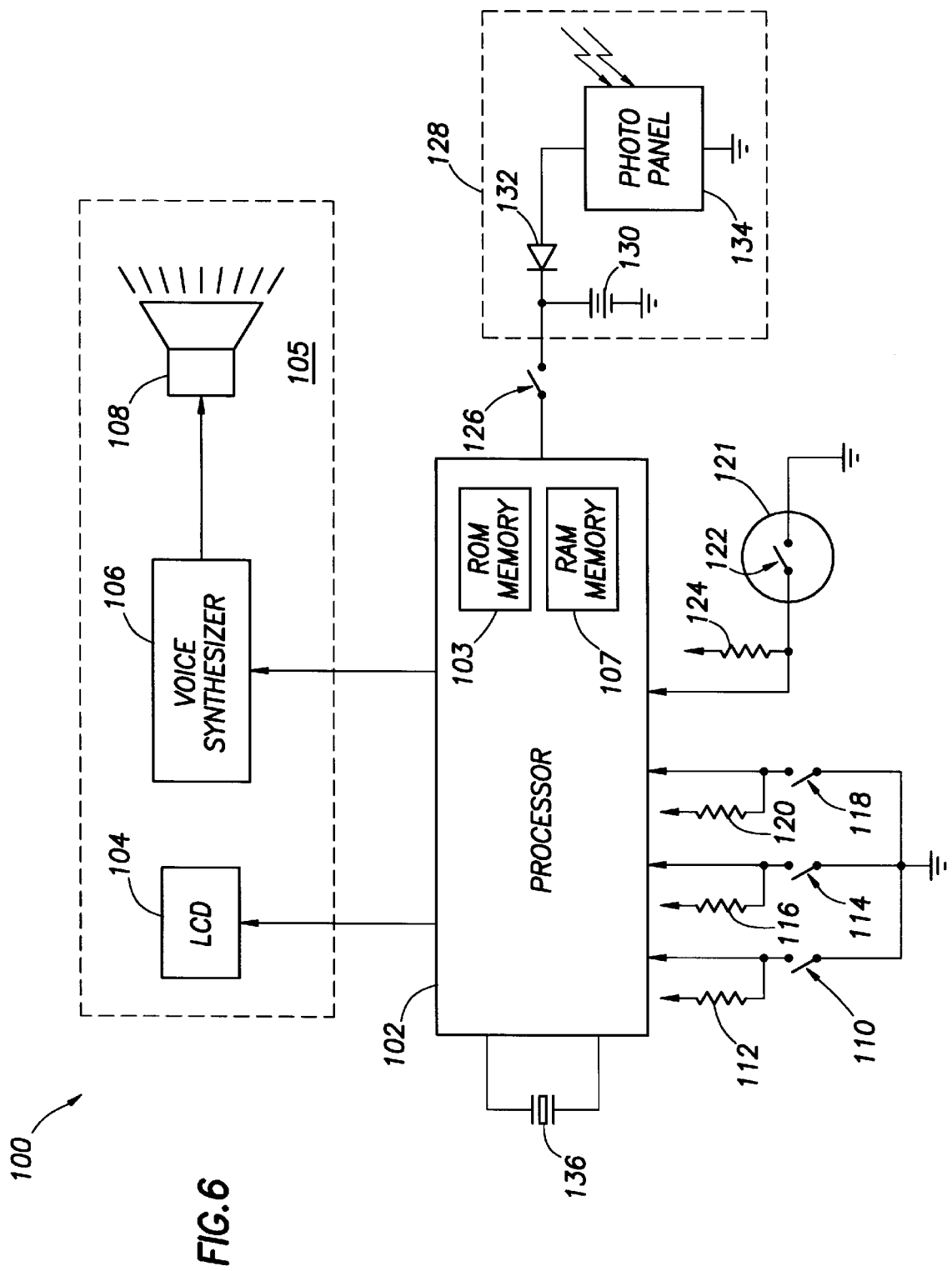

TRAINING UNIT FOR THE PACEMAKER EMERGENCY INTERVENTION SYSTEM USING MAGNETIC ENTRY CODE

BACKGROUND OF THE INVENTION

1. Field of the Invention

The present invention relates generally to a training unit for the pacemaker emergency intervention system. Further still, the invention relates to a training unit that provides instructions, coaching, and feedback to a health care provider regarding the pacemaker emergency intervention system.

2. Background of the Invention

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood from the body. The oxygenated blood from the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, "asynchronous" (fixed rate), "inhibited" (stimulus generated in the absence of a specified cardiac activity), or "triggered" (stimulus delivered in response to a specified hemodynamic parameter). Broadly speaking, the inhibited and triggered pacemakers may be grouped as "demand" type pacemakers, in which a pacing pulse is only generated when demanded by the heart. To determine what pacing rate is required of the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations (or "modes") are usually identified according to a code comprising three or four letters. A fifth coded position may sometimes be used to describe a pacemaker's ability to respond to abnormally high heart rates (referred to as tachycardia). Because most pacemakers do not provide any antitachycardia functions, the fifth coded position is not used in most commonly used pacemaker types. Thus, most common configuration codes comprise either three or four letters, as shown in Table I below. For this reason and for simplicity's sake, the fifth code position is omitted from the following table. Each code can be interpreted as follows:

TABLE I

| PACEMAKER CODE DESCRIPTIONS | | | | |
| --- | --- | --- | --- | --- |
| Code position | 1 | 2 | 3 | 4 |
| Function Identified | chamber paced | chamber sensed | response to sensing | programmability, rate modulation |
| Options Available | O—none A—atrium V—ventricle D—dual (A + V) | O—none A—atrium V—ventricle D—dual (A + V) | O—none T—triggered I—inhibited D—dual (T + I) | O—none P—programmable M—multiprogrammable C—communicating R—rate modulating |

As illustrated in Table I, pacemakers can be programmed or designed to operate in any one of numerous modes of operation. For example, a DDD pacer paces either chamber (atrium or ventricle) and senses in either chamber. Thus, a pacer in DDD mode, may pace the ventricle in response to electrical activity sensed in the atrium. A VVI pacer paces and senses in the ventricle, but its pacing is inhibited by spontaneous electrical activation of the ventricle (i.e., the ventricle paces itself naturally). In VVIR mode, ventricular pacing is similarly inhibited upon determining that the ventricle is naturally contracting. With the VVIR mode, the pacer's pacing rate, however, in the absence of naturally occurring pacing, is modulated by the physical activity level of the patient. Pacers commonly include accelerometers to provide an indication of the patient's level of physical activity. Further still, valid pacemaker modes also include DOO, VOO, AOO, to name but a few.

A complication may arise when a patient with an implanted pacemaker is admitted into a medical facility such as an emergency room. If the patient is experiencing a cardiac-related problem, the examining physician may need to ascertain the mode of operation of the pacemaker in order to diagnose and treat the underlying problem. The patient may not know the mode of operation of his or her pacemaker, and there may not be time for the medical staff to contact the surgeon that implanted the pacemaker or the patient's cardiologist to determine the operational mode programmed for that pacemaker. Even if the initial operational mode of the pacemaker could be ascertained from prior health care professionals, many pacemakers are capable of automatically changing from one mode to another depending on the patient's cardiac needs. Thus, even the surgeon that implanted the pacemaker may have no way of knowing the current operational mode of the patient's pacemaker.

In some instances, however, it is possible to determine the current operational mode of the pacemaker by examining the patient's surface electrocardiogram ("ECG"). A surface ECG, in which adhesive electrodes are placed at various locations on the patient's skin for monitoring the electrical activity of the heart, is commonly performed in medical facilities and, in particular, emergency rooms to determine the physiologoical status of the patient's heart. When a pacemaker emits a pacing pulse to stimulate the heart to beat, that pacing pulse typically manifests itself as a spike on the surface ECG waveform. Thus, it is ocassionally possible to determine the operational mode of the pacemaker by monitoring the pacing spikes on the surface ECG waveform. Some modes of pacemaker operation, however, are so complex that it is nearly impossible to determine the mode of the pacemaker by examining the patient's surface ECG. Even when such a determination is possible, it usually requires a highly specialized physician that may not be available when emergency treatment is needed. Nevertheless, in order to diagnose and properly treat a patient, the need remains for determining the operational mode of an unknown implanted pacemaker quickly and accurately during emergency treatment.

Many pacemakers today have the capability of transmitting information between the implanted pacemaker and an external monitoring device. The communication link typically is bi-directional, permitting data and control signals to be transmitted from the external device to the implanted pacemaker and data to be transmitted by the pacemaker to the external device. Thus, theoretically, a physician or medical technician could determine the operational mode of the pacemaker by using a suitable external monitoring device to request operational mode information from the implanted pacemaker. Although, this approach is theoretically sound, to date it has not been practical because the communication link between an implanted pacemaker and an associated external monitor is customized by each manufacturer. This means that an external monitor manufactured by one pacemaker supplier could not be used to communicate with a pacemaker provided by a different supplier. Consequently, this approach would require the medical facility to have available monitors provided by every pacemaker manufacturer, an absorbatently costly solution. Even if the medical facility had the resources to purchase and maintain external monitors from each pacemaker manufacturer, the examining physician would not know which external monitor to use because he would not know which manufacturer made the pacemaker implanted in the patient.

To remedy this problem, an industry standard has been proposed by the International Organization for Standarization. The standard, entitled ISO/WD 14994, Implants for Surgery-Cardiac Pacemakers-Pacemaker Emergency Intervention System (hereinafter referred to as "PEIS"), requires that all pacemakers manufactured in compliance with this standard include a simple, standard operating mode that can be initiated with a common method. This method is explained in detail in the ISO/WD 14994 standard which is incorporated herein by reference (hereinafter the "PEIS standard"). The PEIS is intended for use in hospital and clinic emergency rooms to permit conversion of conforming implanted cardiac pacemakers to a standard mode (e.g., VVI, VOO) when the pacemaker is perceived by the examining physician to be operating in a non-standard way or in a way not understood by the physician. The PEIS standard refers to the standard operational mode of the pacemaker as the "emergency inhibited mode." Although, the PEIS does not inform the physician of the current pacemaker mode, it does permit the physician to transition any pacemaker (that conforms to the standard) from any mode of operation to a known, simple mode. Once the pacemaker is operating in the known standard PEIS mode, the patient's underlying medical condition can more easily be diagnosed.

As shown in FIGS. 2 and 3, a PEIS assembly 20 defined by the PEIS standard includes a base 22 and a handle 24 attached to the base 22. Base 22 and handle 24 both are constructed of nonmagnetic material, such as plastic. The base 22 includes a bottom surface 26. An annular magnet 30 (FIG. 3) is embedded in the bottom surface 26 of base 22 in accordance with the PEIS standard.

The annular PEIS magnetic 30 has the capability to actuate circuits within a conforming pacemaker, thereby changing the pacemaker's functions to a simple standard mode of operation. The PEIS assembly 20 preferably is mounted on a wall in the vicinity of patients that may need the PEIS. When the examining physician determines that the patient's pacemaker should be placed in the PEIS standard mode of operation, the physician or other medical technician removes the PEIS assembly 20 from the wall and places it on the patient's chest on the site over the implanted pacemaker. This action initiates the "entry code" of the PEIS standard. The implanted pacemaker includes a magnetic field sensor which detects the presence or absence of annular PEIS magnet 30. The PEIS entry code signals the implanted pacemaker to change its mode of operation to the PEIS standard mode. The physician completes the entry code by holding the PEIS assembly 20 in place and then removing it, and repeating this process as illustrated in FIG. 4. The entry code 21 of FIG. 4 takes approximately 13 seconds to complete and includes five steps, each step lasting a predetermined period of time. In the first step 21$a$, the magnetic is placed on the pacemaker site for 3±1 seconds. The magnetic field sensor in the implanted pacemaker detects the presence of the PEIS magnet 30 and a microprocessor, or other device internal to the pacemaker, measures the period of time in which the magnet is held in place. In step 21$b$, the magnet 30 is removed from the patient's chest by the physician by a distance of at least 30 centimeters for 2±1 second. The implanted device also measures this period of time. Steps 21$a$ and 21$b$ are repeated in steps 21$c$ and 21$d$. Finally, the PEIS magnet 30 is placed on the patient for 3±1 seconds in step 21$e$ and then removed. At this point, the physician has provided the entry code to the implanted pacemaker. The pacemaker determines when the magnet is in place and removed, measures the associated time intervals, and if each time interval corresponds to the PEIS standard entry code illustrated in FIG. 4, the pacemaker transitions its current mode of operation to the standard mode required by the PEIS standard. If, however, the correct timing for the entry code has not been provided by the examining physician, the pacemaker will not enter into PEIS standard mode and will remain in its current mode of operation.

According to the PEIS standard, the emergency inhibited mode generally is a VVI mode with a base heart rate of 60±1 pulses per minute ("ppm"). This means that the pacemaker should pace a ventricular chamber at a rate of 60 ppm, but inhibit pacing if the ventrical is able to beat on its own at the target 60 ppm rate. The pacemaker's PEIS emergency inhibited mode also requires the pacemaker to produce a secondary pacing pulse separated from the primary pacing pulse by 80±10 milliseconds ("ms"). This secondary output pulse will have no effect on the cardiac tissue because the secondary pulse will occur at such a time after the primary pulse that the cardiac tissue will not be able to be restimulated by a new pulse. The 80±10 ms spacing is also sufficient to preclude the pacemaker from emitting a secondary pulse in the "vulnerable" period of the cardiac cycle in which a pacemaker pulse could initiate a harmful, and possible lethal, arrhythmia.

Both the primary and secondary pacemaker pulses are visible on the surface ECG. The purpose of the secondary pulse is to provide a visual feedback, via the surface ECG, to the examining physician that the pacemaker has responded to the entry code and is currently in the emergency inhibited mode of operation specified by the PEIS standard. Once the entry code is complete, the pacemaker should then be in a simple mode of operation that is verifiable by the examining physician by monitoring the surface ECG waveform.

When a pacemaker is operating in one of its preprogrammed modes (excluding the PEIS emergency inhibited mode), the PEIS magnet can be used to place the pacemaker in a so-called "magnet mode" of operation. The pacing rate of a pacemaker in the magnet mode is defined by the pacemaker manufacturer. To transition a pacemaker to the magnet mode, the PEIS is placed on the patient's skin over the site of the implanted pacemaker. The pacemaker remains in its magnet mode as long as the PEIS magnet remains on the patient. The pacemaker will revert back to its original mode, however, when the PEIS magnet is removed.

The PEIS standard also requires conforming pacemakers to permit the PEIS magnet to transition the pacemaker from the emergency inhibited mode to an "emergency asychronous mode" in which the pacemaker generates a double pacing pulse (two pulses separated by 80±10 ms) at a base rate of 60±1 ppm. This emergency asychronous mode is initiated after the pacemaker has been placed into the PEIS mode by placing and holding the PEIS magnet in place on the patient's chest over the site of the implanted pacemaker. The pacemaker remains in the emergency asychronous mode as long as the PEIS magnet is held in place on the patient. Pacing is not inhibited while in this mode. When the magnet is removed, the pacemaker will transition back to the emergency inhibited mode.

The PEIS standard requires the magnetic 30 to be a permanent, fixed magnet, and not an electromagnet, which requires electrical power to create the magnetic field. The annular magnet is simple, inexpensive, reliable, and durable. The drawback in requiring a fixed magnet, rather than an electromagnet through which the entry code of FIG. 4 could be automatically generated, is that a human is responsible for ensuring the PEIS magnetic 30 is placed on the patient's chest and removed with the proper timing defined for the PEIS entry code. Although the timing of the entry code is relatively simple, it still requires training to properly and accurately administer the code. Periodic retraining is also necessary. Further still, the examining physician that must initiate the entry code in an emergency situation may not have used the PEIS assembly 20 for an extended period of time, and may need some training in using the PEIS magnetic before attempting to place the patient's pacemaker in the PEIS emergency inhibited mode. Accordingly, the training must be simple and fast.

Thus, a training unit for a PEIS is needed. The training unit should be simple to use and readily available to medical personnel when a patient's pacemaker must be transitioned into the PEIS emergency inhibited mode. Preferably, the training unit should coach the medical professional or technician to perform the entry code and also permit the medical technician to practice the entry code without coaching. Despite the advantages such a training unit would provide, to date no such training unit is known to exist.

SUMMARY OF THE INVENTION

The deficiencies of the prior art described above are solved in large part by a training unit which includes a processor, a magnetic field sensor, a plurality of control switches, and a message and data output device. Placing a PEIS magnet adjacent to or in contact with the training unit activates the magnetic field sensor, a condition detectable by the processor. Activation of the control switches determines in which of three modes the training unit operates. In an instructional mode, the processor provides instructional messages to the operator via the message and data output device, which preferably includes a display and an audio speaker. In a coached mode, the training unit informs the operator when to place the magnet adjacent to or in contact with the training unit and when to remove the magnet in accordance with the timing intervals of the PEIS entry code. In a practice mode, the operator initiates and completes the entry code using a PEIS magnet without coaching. The processor detects the presence of the PEIS magnet, and determines whether the operator performed the entry code correctly.

If the operator successfully completes the entry code in either the coached or practice modes, a simulated ECG waveform indicative of a patient's surface ECG is retrieved from memory by the processor and is shown on the display. Conversely, the training unit informs the operator of a failure by the operator to successfully complete the entry code.

BRIEF DESCRIPTION OF THE DRAWINGS

For a more detailed description of a preferred embodiment of the present invention, reference will now be made to the accompanying drawings, wherein:

FIG. 6 is a block diagram of the training unit in accordance with the preferred embodiment.

DETAILED DESCRIPTION OF PREFERRED EMBODIMENTS

Figure 1:
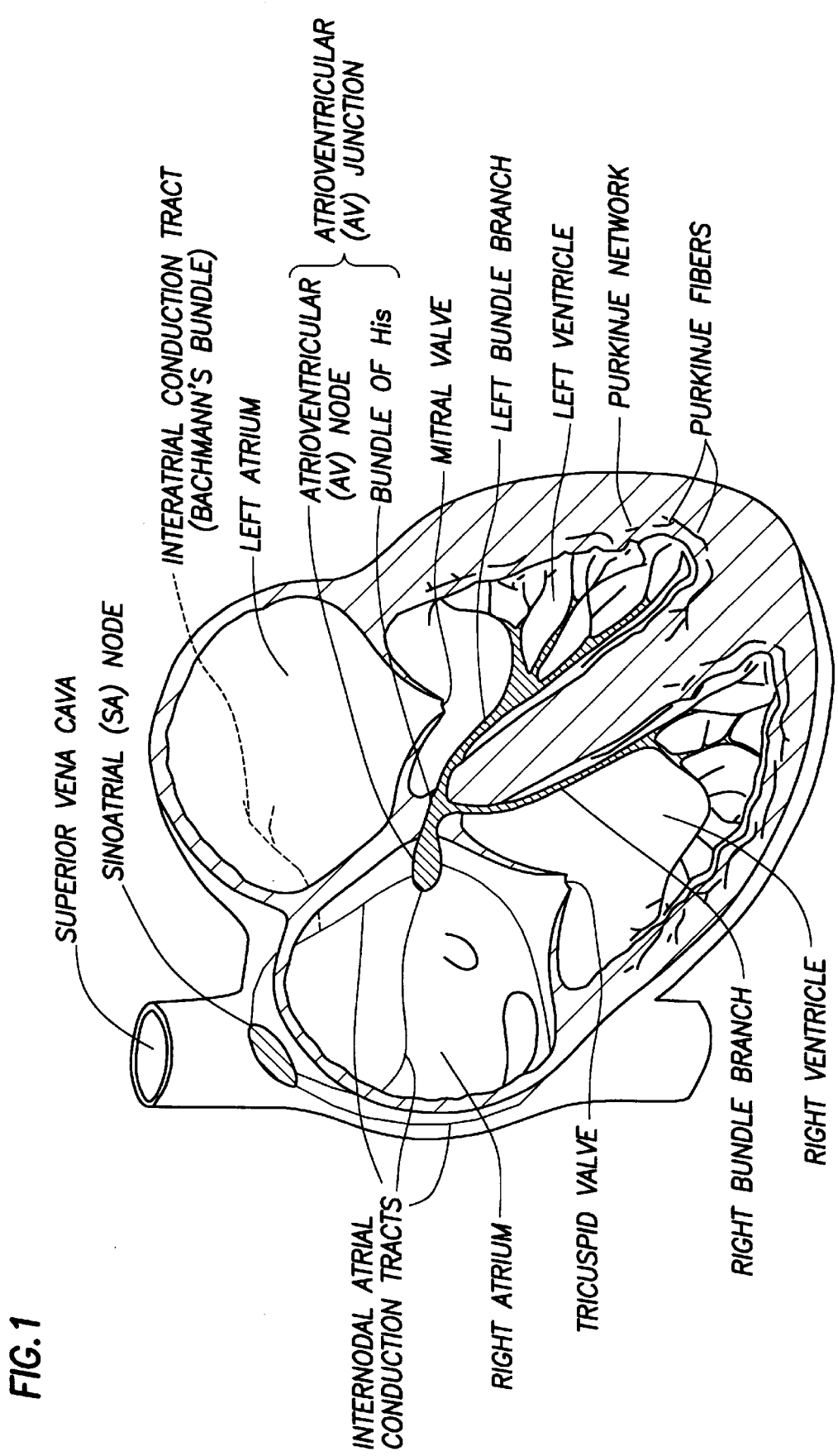
FIG. 1 is a schematic representation of the heart illustrating the relevant cardiac structure.
Figure 2:
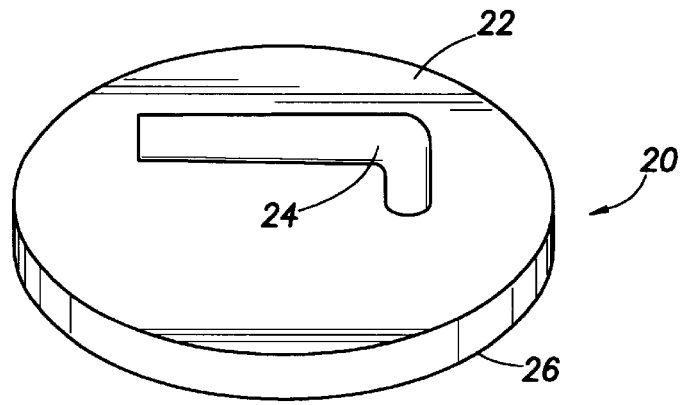
FIG. 2 is a perspective view of a standard PEIS assembly.
Figure 3:
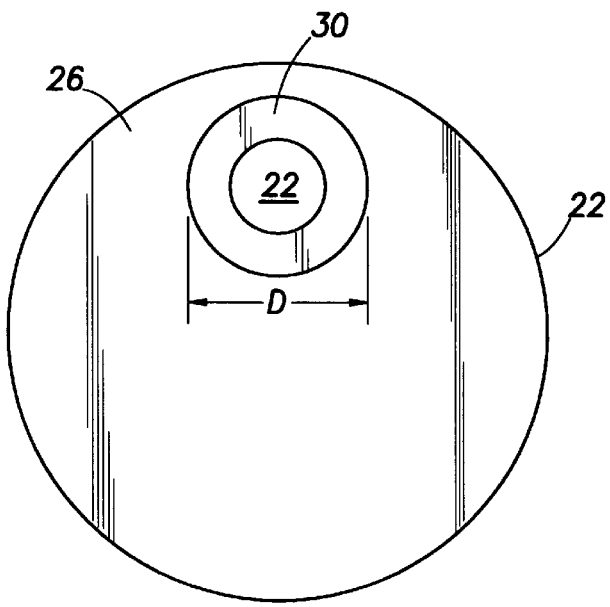
FIG. 3 is a view of the bottom surface of the PEIS assembly of FIG. 2 illustrating the position of the PEIS annular magnet.
Figure 5:
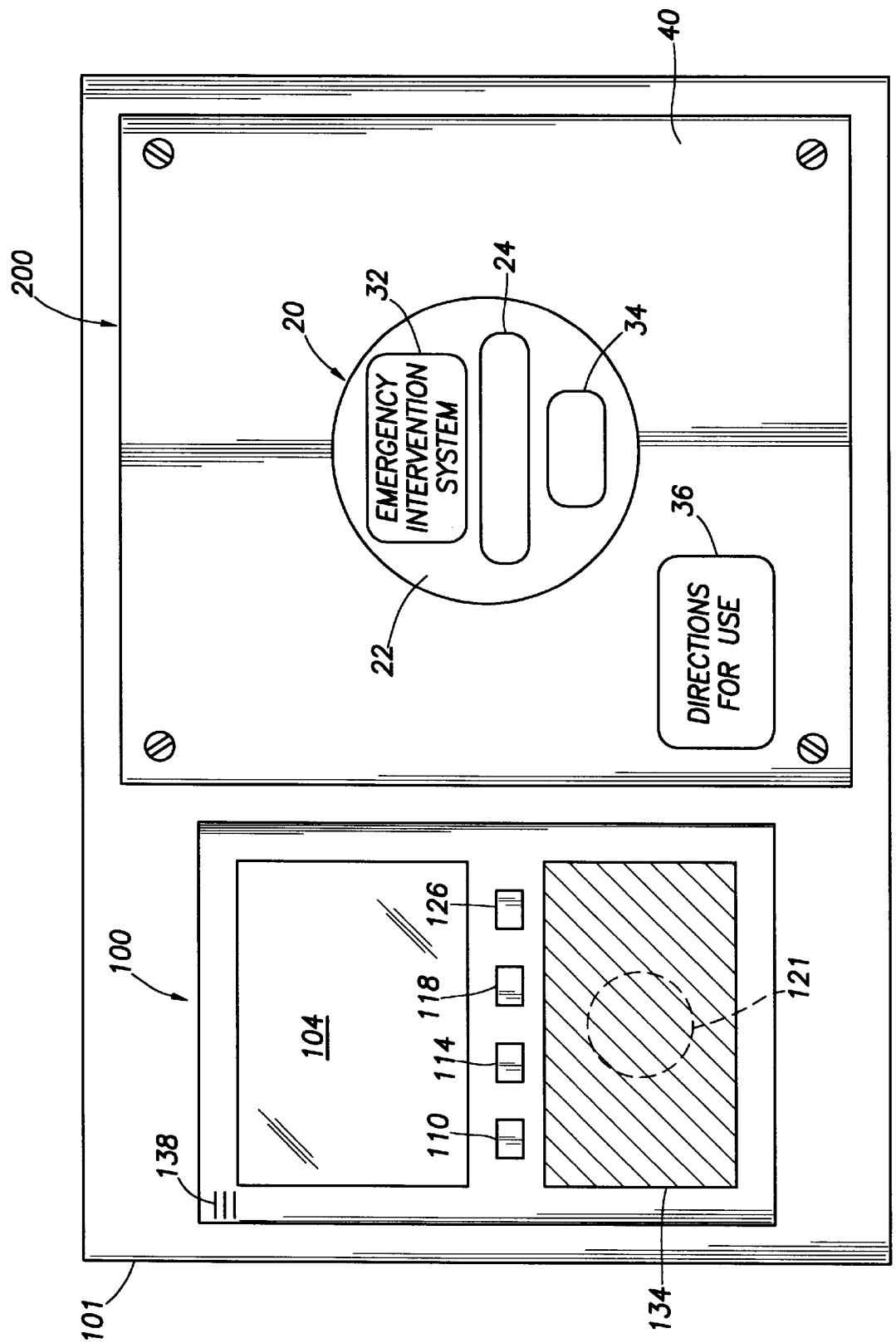
FIG. 5 is an elevation view of the training unit of the present invention and a pacemaker emergency intervention system as mounted on a wall.

Referring now to FIG. 5, a PEIS training unit 100, constructed in accordance with the preferred embodiment, is shown mounted adjacent a PEIS 200. PEIS 200 generally includes a PEIS assembly 20 mounted on a magnetic plate 40. As illustrated in FIGS. 2 and 3, PEIS assembly 20 includes a non-magnetic base 22 and a non-magnetic handle 24. A fixed magnet is embedded in the bottom surface 26 (FIG. 3), but is not specifically shown in FIG. 5. The magnet 30 holds the PEIS assembly 20 to the magnetic plate 40. Thus, to remove the PEIS assembly 20 from the magnetic plate 40, the PEIS assembly 20 is simply pulled away from magnetic plate 40 with a force sufficient to overcome the magnetic attraction between the magnet 30 and magnetic plate 40. The PEIS standard specifies that the magnetic field strength of magnet 30 is in the range of 90 to 120 Gauss at a distance of 2 cm from the magnet. The PEIS assembly 20 also includes labels 32 and 34 and magnetic plate 40 includes a label 36. These labels are preferred by the PEIS standard.

Training unit 100 preferably is mounted in close proximity to PEIS 200 and generally includes a display 104, controls 110, 114, 118, 126, a photovoltaic panel array 134, and a speaker cover 138. Both the training unit 100 and PEIS 200 preferably are mounted on a common support mechanism 101 which is mounted on a wall in close proximity to patients that may need the use of the PEIS 200.

Training unit 100 also includes a magnetic sensor 121 shown in dashed outline in FIG. 5 and described in greater detail with respect to FIG. 6. The magnetic sensor 121 may be mounted on or included within the training unit 100. As shown in FIG. 5, the magnetic sensor is mounted behind the photovoltaic panel array 134, but may be mounted in other locations within training unit 100 as desired. Controls 110, 114, 118, 126 provide an operator (such as a physician or other health care provider) control over the training unit 100. Controls 110, 114, 118, 126 may be any suitable type of control such as a push button switch, a toggle switch, a slide switch, a capacitive touch pad, or a heat sensitive switch, as examples. As will be explained in greater detail below, training unit 100 includes three modes of operation. Each of the modes of operation are initiated by one of the switches 110, 114, 118. Switch 126 is a power switch for turning the training unit 100 on and off.

Display 104 is any suitable type of display for providing feedback to the operator during operation of the training unit 100. In accordance with the preferred embodiment, display 104 comprises a liquid crystal display ("LCD") such as a DMF-5002N manufactured by Optrex. Display 104 should be sufficiently large to permit multiple lines of status information to be presented to the operator simultaneously. Display 104 should also permit graphical representations to be displayed such as ECG waveforms.

A speaker 108, (FIG. 6) is included within training unit 100. Speaker cover 138 protects the speaker 108 and permits effective transmission of sound from the speaker 108 to the operator.

Photovoltaic panel array 134 converts light energy into electrical energy in accordance with known techniques. The electrical energy produced by photovoltaic panel array provides the operational power for the training unit 100. Thus, training unit 100 need not be plugged into the wall for electrical power. Accordingly, training unit 100 can advantageously be located anywhere desired without regard to the location of electrical outlets. Photovoltaic panel array can be any suitable array such as Sunceram II series manufactured by Panasonic. Alternatively, power for the training unit can be provided by the building power distribution system in accordance with known techniques.

Referring now to FIG. 6, training unit 100 constructed in accordance with the preferred embodiment includes a processor 102, a message and data output device 105, a plurality of switches 110, 114, 118, and 126, a magnetic field sensor 121, a power supply 128, and a frequency oscillator 136. The processor 102 generally controls the operation of the training unit 100. Switches 110,114,118 connect to the processor and are used to control the operational state of the training unit 100.

Any suitable device can be used as the processor 102. For example, processor 102 may include a PIC17C756 manufactured by Microchip. Training unit 100 preferably also includes read only memory (ROM) and random access memory (RAM) either internal or external to processor 102. The exemplary processor 102 of FIG. 6 is shown to include ROM 103 and RAM 107. The ROM memory stores software to be executed by processor 102. This software is explained in greater detail below. The processor 102 executes a portion or all of the software by copying the desired portion of the software to the RAM memory and executes the software from RAM in accordance with conventional techniques.

The message and data output device 105 provides feedback information to the operator of the training unit. The feedback information preferably includes visual status messages and graphical representations, but may also include audible tones and speech. Accordingly, message and data output device 105 may include a display 104, a voice synthesizer 106, speaker 108, or any other suitable feedback device. Voice synthesizer 106 may include a DT1050 Voice Synthesizer chip set manufactured by National Semiconductor suitable for causing speaker 108 to produce audible feedback such as status tones and human speech. Speaker 108 preferably is a micro speaker device such as EAS-4P15SA manufactured by Panasonic.

Magnetic field sensor 121 preferably includes a magnetic reed switch 122 known to those of ordinary skill in the art. A normally-open magnetic reed switch closes in response to the presence of a magnetic field of sufficient strength. Otherwise, the magnetic reed switch remains in the open state as shown in FIG. 6. Magnetic reed switch 122 connects to the processor 102 via a pull-up resistor 124. Accordingly, when the magnetic reed switch 122 is in the open state as shown in FIG. 6 (insufficient magnetic field strength to close the switch), the input signal from the switch 122 to the processor 102 is pulled to a logic high level by the pull-up resistor 124. However, when a magnetic field of sufficient strength causes the magnetic reed switch 122 to close, the signal from the magnetic reed switch 122 to the processor 102 falls to the logic low state. Thus, by monitoring the signal from the magnetic reed switch 122, the processor 102 can determine when a magnet is placed close to the training unit 100. Using another scheme, a normally-closed switch could suitably be employed.

The normally-open magnetic reed switch 122 selected to be used as magnetic field sensor 121 is suitable for detecting the presence of PEIS magnetic 30 when PEIS assembly 20 is removed from plate 40 of PEIS 200 and placed in close proximity to the magnetic field sensor 121. In the exemplary embodiment of FIG. 5, processor 102 detects the presence of the PEIS magnet 30 (FIG. 3) when the operator places the bottom surface 26 of PEIS assembly 20 close to or in contact with photovoltaic panel away 134, beneath which is located magnetic field sensor 121.

Referring again to FIG. 6, power supply 128 provides electrical power for operating the processor 102 and other components of the training unit 100. Power supply 120 preferably includes a rechargeable battery 130, a diode 132, and a photovoltaic panel 134. Photovoltaic panel 134 generally includes an array of photovoltaic cells (not shown) and generates an electrical current in response to light impinging on the panel's photovoltaic cells. Photovoltaic panel 134 preferably provides sufficient electrical current through diode 132 to the rechargeable battery 130 to maintain the rechargeable battery 130 in a fully charged state. Power for the training unit 100 is derived generally from the rechargeable battery 130 which is continuously recharged by the photovoltaic panel 134. Switch 126 is a power switch used to turn power on and off to the training unit 100. With the power switch 126 in the open position as shown in FIG. 6 power is disabled to the training unit 100. Conversely, with the power switch 126 in the closed position the training unit 100 is powered on by the rechargeable battery 130.

Frequency oscillator 136 provides a clock signal to processor 102 to control the timing of the processor, as would be understood by one of ordinary skill in the art. As described above, the processor 102 includes on-board ROM and RAM memory. The processor 102 executes instructions permanently stored in the ROM memory. These instructions comprise the training unit's software, the function of which is described in greater detail below.

The training unit 100 preferably includes three modes of operation. Each mode of operation is initiated by one of the switches 110, 114, and 118. In accordance with the preferred embodiment, the training unit 100 includes the following modes of operation: instructional mode, coached mode, and practice mode. Activating switch 110 preferably initiates the instructional mode. Activating switch 114 preferably initiates the coached mode, and activating switch 118 initiates the practice mode.

When the training unit 100 is turned on by activating the power switch 126, the processor 102 preferably initiates the instructional mode automatically. The training unit 100 may then be transitioned to one of the other two modes (i.e., the coached mode or practice mode) by pressing one of the switches 114, 118. The instructional mode may be re-entered by pressing switch 110. Further, whenever an operator wishes to initiate any one of the three modes of operation, the user simply presses the desired switch 110, 114, 118. The processor 102 detects when and which switch is pressed and, in response, loads appropriate software instructions into RAM memory for execution by the processor, in accordance with conventional techniques. The functions performed by the training unit 100 for each mode are described below and are dictated primarily by the software that is loaded into RAM memory when a control switch 110, 114, 118 is pressed. Alternatively, discrete circuits could be provided to implement the operational modes described below.

In the instructional mode, the training unit 100 teaches the operator about the purpose of the PEIS, magnet modes of pacemakers, how to execute the entry code, the appearance of the surface ECG after the entry code has been successfully transmitted and the implanted pacemaker enters the PEIS emergency inhibited mode, and anything else desired. These instructions may be presented visually via LCD display 104 and/or audibly via speaker 108.

Figure 4:
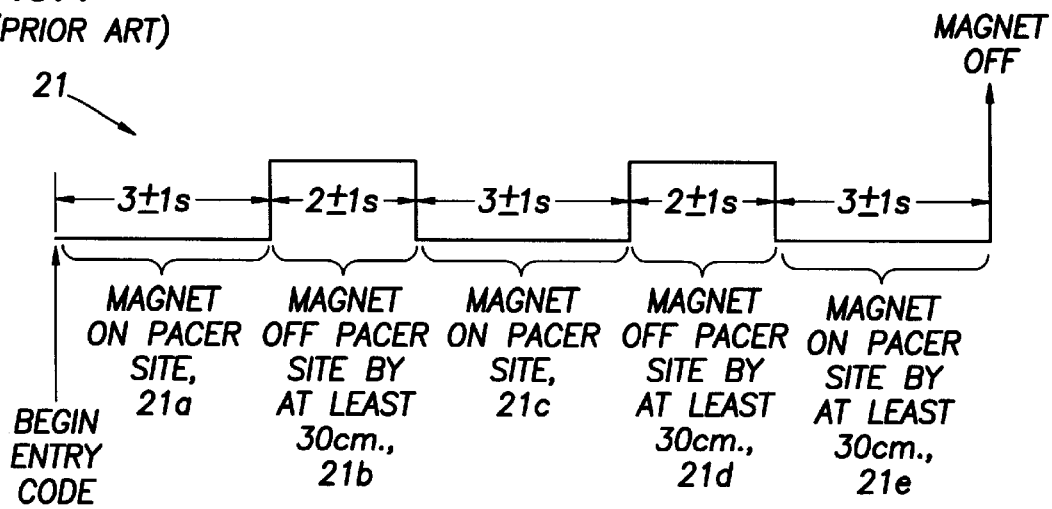
FIG. 4 illustrates the entry code specified by the pacemaker emergency intervention system standard.

In the coached mode of operation, an operator can practice the PEIS entry code (FIG. 4) with coaching from the training unit 100. When switch 114 is activated, the operator will be prompted by a message on LCD display 104 and/or by an audible message from speaker 108 to place the PEIS magnet assembly 20 sufficiently close to the magnetic field sensor 121 to activate the sensor 121 to begin the entry code 21. The operator will then be prompted, via LCD display 104 and/or speaker 108, to keep the PEIS magnetic assembly 202 in close proximity to the training unit 100 for 3±1 seconds (portion 21a in FIG. 4). Then, the operator will be prompted to remove the magnetic assembly 20 for 2±1 seconds (portion 21b), and continue with the process defined by portions 21c, 21d, 21e of the entry code 21 of FIG. 4. The coached mode thus steps the operator through the entry code 21 and provides feedback to the operator if the timing required by the entry code is not satisfied. The operator can repeat the coached mode by again pressing the switch 114 on the training unit 100.

The practice mode of operation permits the operator to practice an entry code 21 without coached feedback from the training unit. The operator initiates the practice mode by pressing switch 118. A message is then presented visually on LCD display 104 and/or audibly via speaker 108 for the operator to begin the entry code 21. At this point, the operator uses the PEIS assembly 20 from PEIS 200 to initiate and complete a PEIS entry code 21. Processor 102 preferably determines whether the operator has met the timing constraints defined by the entry code 21 and provides visual and/or audible feedback to the operator indicating whether the operator was successful.

Once the entry code 21 has been successfully completed in either the coached or practice modes, a simulated surface ECG waveform is displayed on LCD display 104 to show the operator the effect of the PEIS on an implanted pacemaker. The simulated ECG waveform preferably is digitally stored in the ROM memory discussed above with respect to FIG. 6. If the operator feels further coaching is necessary, the operator may wish to initiate the coached mode described above. If no further instruction or practice is necessary, the operator is ready to use the PEIS in conjunction with a patient.

Thus, training unit 100 provides training on the use of the PEIS. The training unit is easy and quick to use and provides the operator with coached or uncoached practice in the generation of the PEIS entry code.

Numerous variations and modifications will become apparent to those skilled in the art once the above disclosure is fully appreciated. It is intended that the following claims be interpreted to embrace all such variations and modifications.

What is claimed is:

1. A training unit adapted to be used in conjunction with a pacemaker emergency intervention system (PEIS), the PEIS including a magnet that can be used to implement an entry code, having a plurality of predetermined timing intervals, said training unit including:

a processor;

a message and data output device coupled to said processor; and a magnetic field sensor coupled to said processor and adapted to provide a signal to said processor indicative of the presence of a magnetic field sufficiently strong to activate said magnetic field sensor during some of the predetermined timing intervals;

said processor determining whether a magnetic field has activated said magnetic field sensor during substantially the entirety of at least one of said predetermined timing intervals.

2. The training unit of claim 1 wherein said training unit includes an instructional mode of operation wherein instructional messages are provided by said processor to an operator via said message and data output device.

3. The training unit of claim 2 further including a coached mode of operation in which said processor provides messages to said message and data output device to coach an operator through said entry code.

4. The training unit of claim 3 further including a practice mode of operation in which said processor determines whether the operator has completed the entry code successfully.

5. The training unit of claim 4 further including a memory device in which is stored a digital representation of an exemplary surface ECG waveform indicative of a pacemaker in an emergency PEIS mode of operation.

6. The training unit of claim 5 wherein said ECG waveform is retrieved from said non-volatile memory by said processor and provided to said message and data output device after said coached or practice modes are successfully completed.

7. The training unit of claim 1 wherein said entry code includes first, second, third, fourth, and fifth timing intervals and said processor determines whether the magnetic field activates said magnetic field sensor during substantially the entirety of said first timing interval.

8. The training unit of claim 7 wherein said processor determines whether the magnetic field activates said magnetic field sensor during substantially the entirety of said third and fifth timing intervals.

9. The training unit of claim 8 wherein said first, third, and fifth timing intervals are 3±1 seconds long.

10. The training unit of claim 8 wherein said processor determines whether the magnetic field sensor is deactivated during substantially the entirety of said second and fourth timing intervals.

11. The training unit of claim 10 wherein said second and fourth timing intervals are 2±1 seconds long.

12. The training unit of claim 11 further including a plurality of control switches coupled to said processor for selecting one of said instructional, coached, and practice modes.

13. The training unit of claim 11 further including a power supply comprising a rechargeable battery and a solar panel.

14. The training unit of claim 1 wherein said magnetic field sensor comprises a magnetic read switch.

15. A method for training an operator in the use of a pacemaker emergency intervention system (PEIS) to initiate and complete an entry code, comprising:

monitoring a control switch;

initiating a coached mode of operation when said control switch is activated;

informing the operator when to position a PEIS magnet in close proximity to a training unit;

measuring a time interval associated with said entry code; and informing the operator when to remove the PEIS magnet from said training unit.

16. The method of claim 15 further including measuring a plurality of time intervals associated with said entry code.

17. The method of claim 16 further providing feedback to the operator as to whether said time intervals associated with said entry code have been satisfied.

18. The method of claim 17 wherein providing feedback includes displaying a simulated ECG waveform.

19. A method for training an operator in the use of a pacemaker emergency intervention system (PEIS) to initiate and complete an entry code, comprising:

monitoring a control switch;

measuring a plurality of timing intervals defined by the presence and absence of a magnetic field;

comparing said timing intervals to predetermined timing values; and informing the operator as to whether the timing intervals substantially match said predetermined timing values.

20. The method of claim 19 wherein said predetermined timing values include first, second, third, fourth, and fifth predetermined timing values.

21. The method of claim 20 wherein said first, third, and fifth predetermined timing values are 3±1 seconds.

22. The method of claim 21 wherein said second and fourth predetermined timing values are 2±1 seconds.

23. The method of claim 19 wherein said informing step includes displaying a simulated ECG waveform.

24. A training unit adapted to be used in conjunction with a pacemaker emergency intervention system (PEIS) that includes a magnet to an implanted pacemaker for implementing an entry code comprising first, second, third, fourth, and fifth timing intervals, said training unit including:

a control device;

a display coupled to said control device; and a magnetic field sensor coupled to said control device and providing a signal to said control device indicative of the presence of a magnetic field sufficiently strong to activate said magnetic field sensor;

said control device determining whether a magnetic field has activated said magnetic field sensor during substantially the entirety of the first, third, and fifth timing intervals.

25. The training unit of claim 24 wherein said magnetic field sensor comprises a magnetic reed switch.

26. The training unit of claim 24 further including a plurality of control switches for selecting an operational mode.

* * * * *

UNITED STATES PATENT AND TRADEMARK OFFICE
CERTIFICATE OF CORRECTION

PATENT NO.   : 5,873,733
DATED        : February 23, 1999
INVENTOR(S)  : Paul et al.

It is certified that error appears in the above-identified patent and that said Letters Patent is hereby corrected as shown below:

Column 10,
Lines 56-57, delete "predetermined timing intervals" and insert -- said PEIS Standard timing intervals --, therefor.

Column 11,
Line 13, delete "the", second occurrence, and insert -- said --, therefor.
Line 20, delete "non-volatile".
Line 51, delete "an entry code" and insert -- a PEIS Standard entry code --, therefor.

Column 12,
Line 3, 8 and 11, delete "said entry code" and insert -- said PEIS Standard entry code --, therefor.
Line 16, delete "an entry code" and insert -- PEIS Standard entry code --, therefor.
Lines 20-21, delete "predetermined timing values" and insert -- PEIS Standard timing values --, therefor.
Line 23, delete "predetermined timing values" and insert -- PEIS Standard timing values --, therefor.
Lines 24-25, delete "predetermined timing values" and insert -- PEIS Standard timing values --, therefor.
Line 26, delete "predetermined timing values" and insert -- PEIS Standard timing values --, therefor.
Line 28, delete "predetermined timing values" and insert -- PEIS Standard timing values --, therefor.
Line 30, delete "predetermined timing values" and insert -- PEIS Standard timing values --.
Line 35, delete "magnet to an implanted" and insert -- magnet for communication with an implanted --, therefor.

UNITED STATES PATENT AND TRADEMARK OFFICE
CERTIFICATE OF CORRECTION

PATENT NO. : 5,873,733
DATED : February 23, 1999
INVENTOR(S) : Paul et al.

It is certified that error appears in the above-identified patent and that said Letters Patent is hereby corrected as shown below:

<u>Column 12 cont'd,</u>
Line 36, delete "an" and insert -- a standard --, therefor.
Line 46, insert -- said -- preceding "first".

Signed and Sealed this

Sixteenth Day of April, 2002

Attest:

JAMES E. ROGAN
*Attesting Officer*    *Director of the United States Patent and Trademark Office*